United States Patent
Magee et al.

[11] Patent Number: 5,957,927
[45] Date of Patent: Sep. 28, 1999

[54] BONE FIXATION DEVICE INTRODUCER

[75] Inventors: Christopher Michael Magee, Exton; Sean Hamilton Kerr, Collegeville, both of Pa.

[73] Assignee: Synthes (USA), Paoli, Pa.

[21] Appl. No.: 09/028,273

[22] Filed: Feb. 24, 1998

[51] Int. Cl.⁶ .................................................. A61B 17/88
[52] U.S. Cl. .............................. 606/99; 606/104; 606/69; 606/72
[58] Field of Search ................................ 606/69, 70, 71, 606/99, 101, 96, 104, 205

[56] References Cited

U.S. PATENT DOCUMENTS

| | | | |
|---|---|---|---|
| D. 320,414 | 10/1991 | Morgan | D20/22 |
| 3,856,016 | 12/1974 | Davis . | |
| 4,471,766 | 9/1984 | Terayama . | |
| 4,502,475 | 3/1985 | Weigle et al. | 606/105 |
| 4,854,302 | 8/1989 | Allred, III . | |
| 4,923,471 | 5/1990 | Morgan | 623/16 |
| 4,959,065 | 9/1990 | Arnett et al. | 606/69 |
| 4,994,910 | 2/1991 | Williams | 358/98 |
| 5,199,417 | 4/1993 | Muller et al. . | |
| 5,334,150 | 8/1994 | Kaali | 604/164 |
| 5,373,840 | 12/1994 | Knighton . | |
| 5,377,668 | 1/1995 | Ehmsen et al. . | |
| 5,423,826 | 6/1995 | Coates et al. | 606/96 |
| 5,558,669 | 9/1996 | Reynard | 606/15 |
| 5,569,160 | 10/1996 | Sauer et al. | 600/114 |
| 5,641,287 | 6/1997 | Gittleman | 433/75 |
| 5,658,236 | 8/1997 | Sauer et al. | 600/114 |
| 5,667,475 | 9/1997 | Laser et al. | 600/127 |
| 5,667,478 | 9/1997 | McFarlin et al. | 600/182 |
| 5,690,631 | 11/1997 | Duncan et al. | 606/69 |
| 5,700,267 | 12/1997 | Urbanski | 606/86 |
| 5,700,275 | 12/1997 | Bell et al. | 606/208 |
| 5,702,463 | 12/1997 | Pothier et al. | 623/20 |
| 5,725,523 | 3/1998 | Mueller | 606/15 |
| 5,732,992 | 3/1998 | Mauldin | 294/119.1 |

*Primary Examiner*—Michael Buiz
*Assistant Examiner*—David O. Reip
*Attorney, Agent, or Firm*—Pennie & Edmonds LLP

[57] ABSTRACT

A surgical tool for assisting the implantation of a bone fixation device is disclosed. The tool includes a bone fixation device holder for releaseably engaging a bone fixation device. The bone fixation device holder has at least one hole which is larger in diameter than the bone fixation device screws and aligns with at least one of the bone fixation device screw holes when the bone fixation device is engaged by the bone fixation device holder. The tool also includes a handle proximal to the holder and consisting of left and right portions. As the left and right portions are moveable relative to each other and a distal end of the handle is connected to a proximal end of the holder, the relative movement of the left and right portions results in angular movement of the bone fixation device holder. The tool according to the present invention facilitates the stabilization, fusion, or distraction of bone parts.

18 Claims, 6 Drawing Sheets

BONE FIXATION DEVICE INTRODUCER

FIELD OF THE INVENTION

The present invention is directed to a tool to assist the implantation of an internal bone fixation device.

BACKGROUND OF THE INVENTION

An internal bone fixation device is a medical implant used to stabilize, fuse, or distract bones or bone parts. A bone plate used to stabilize a bone fracture is one example of an internal bone fixation device. Traditionally, the fracture site to be plated is exposed through a large surgical incision. This large incision is required to provide sufficient access for manipulation of the plate and associated fastening instrumentation as well as for adequate visualization. It is often desirable to minimize the size of this incision to reduce scarring and soft tissue trauma. However, due to the small surgical incision of these minimally invasive approaches, it is frequently difficult to gain the access required to expose the fracture site, reduce the fracture, insert the bone plate, and maintain the bone plate in the proper position while it is being attached by screws or other means to the bone parts. While it is not always required, an endoscope may be used to enhance visualization.

The repair of a subcondylar mandible fracture illustrates one procedure in which it is desirable to use a minimally invasive approach. The traditional surgical approach involves a large facial incision in an area proximal to the ear. Such an incision can often lead to facial scarring as well as impaired function of the facial nerve controlling the facial muscles. Despite the size of the incision, gaining sufficient access to the fracture site is still difficult. Therefore, this surgical approach is only employed for the most severe condylar fractures.

Some surgeons have performed this procedure using a minimally invasive approach. In this approach, a small intraoral incision is made for the insertion of a bone plate as well as an endoscope for improved visualization. Soft tissue elevation and retraction also occur through this incision. Due to soft tissue constraints, the intraoral incision must be between the upper and lower gum lines.

As the incision site can be several centimeters from the needed location of the bone plate, inserting the bone plate can be difficult. In addition, the axis of access created by the incision is not parallel to the needed axis of the bone, plate, i.e., perpendicular to the fracture. This further complicates insertion and positioning of the bone plate.

Once the fracture has been reduced and the bone plate is in the proper position, the plate must be attached to the bone. Access to the screw holes is usually by a percutaneous incision made over the fracture site. The percutaneous incision is also useful in reducing the fracture with the aid of a trocar or similar device. It is difficult to maintain the position of the bone plate during the drilling and screwing operations used to fix the bone plate. Locating the screw holes through the percutaneous incision can also be problematic. Once the plate is attached, suturing the two incisions completes the procedure.

Another instance where it would be desirable to plate fractures using a minimally invasive approach includes plating of diaphyseal fractures of long bones. For example, a fracture of the tibia may require a plate with a length of 120–130 mm. Traditionally an incision is made of at least this length, whereby if instrumentation existed for distal holding and manipulation of a plate, the plate could be introduced through an incision little more than the width of the plate and fastened through percutaneous incisions.

As the above discussion illustrates, there exists a need for a tool to assist with the implantation of internal bone fixation devices.

SUMMARY OF THE INVENTION

The present invention relates to an introducer for an internal bone fixation device. This introducer has a fixation device holder on a distal end of the introducer for releaseably engaging an internal bone fixation device. The fixation device holder has several spaced holes which are larger in diameter than the bone screws and align with the bone fixation device screw holes when the bone fixation device is releaseably engaged to the fixation device holder. The spaced holes can be substantially conical in shape to permit insertion of the bone screws at an angle. In one embodiment, the introducer also includes a handle having left and right portions on a proximal end of the introducer. The left and right portions are moveable relative to each other, and a distal end of the handle is connected to a proximal end of the holder so that the relative movement of the left and right portions results in angular movement of the fixation device holder. The handle can have at least one bore for receiving an endoscope so that the introducer can be used in endoscopic procedures.

In a preferred embodiment of the present invention, the fixation device holder has a distal segment connected at a proximal end to two legs. The holder is attached to the handle by the two legs. Preferably, the bottom of the fixation device holder has a recessed area for releaseably engaging the bone fixation device, with the width of the recessed area being slightly less than the width of the bone fixation device.

DESCRIPTION OF THE PREFERRED EMBODIMENTS

In the description which follows, the term "proximal" refers to the end which is closer to the user of the introducer and the term "distal" refers to the end which is further from the user.

Figure 1:
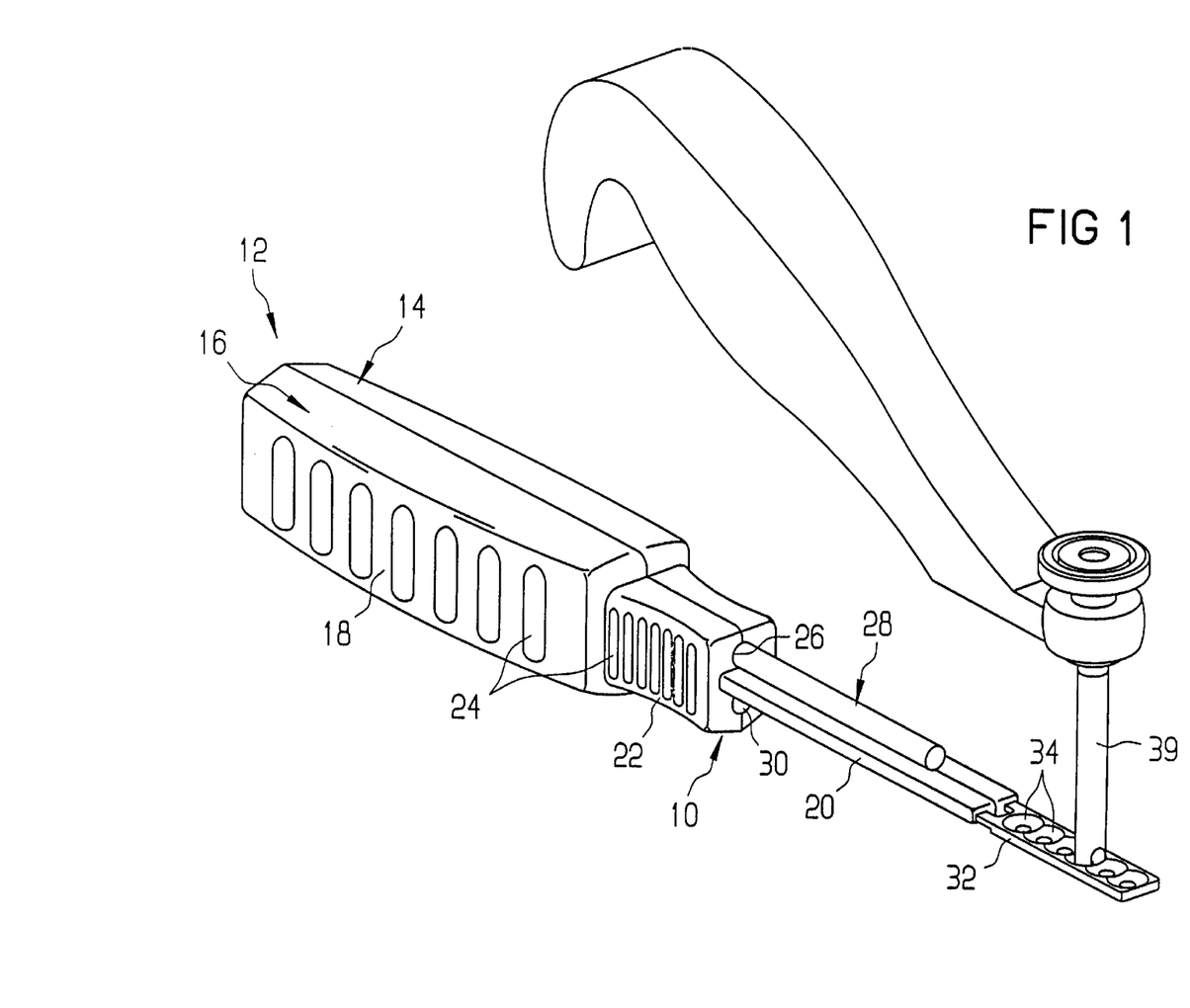
FIG. 1 is a perspective view of a first embodiment of the bone fixation device introducer according to the present invention.

FIG. 1 shows a bone fixation device introducer 10 having a handle 12 that includes a left portion 14 and a right portion 16. Left and right portions 14, 16 are joined in such a fashion that relative movement between left portion 14 and right portion 16 is possible. Handle 12 includes a gripping section 18 located proximal to the user, an extending section 20 located distal to the user, and a connecting section 22 located between gripping section 18 and extending section 20.

Gripping section 18 and connecting section 22 are configured and dimensioned to accommodate the hand and fingers of the user so that ease of use and control are maximized. These sections may include bumps 24 to assist feel and control of introducer 10. Preferably, a bore 26 extends along the length of gripping section 18 and connecting section 22. Bore 26 is sized to receive an endoscope 28. Additionally bores such as bore 30 can also be provided to provide a different field of visualization.

Figure 3:
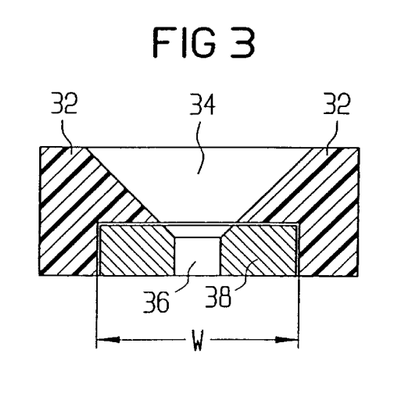
FIG. 3 is a cross-sectional view of a portion of the fixation device holder, taken along line III—III of FIG. 2.

Connected to a distal end of extending section 20 is a bone fixation device holder 32. Holder 32 has several spaced holes 34. As best illustrated in FIG. 3, holes 34 align with screw holes 36 of bone fixation device 38. Holes 34 are larger in diameter than screw holes 36. In fact, although the screw is not shown, holes 34 are larger in diameter than the largest part of the screw, typically the head. This allows holder 32 to be removed from bone fixation device 38 after it has been screwed into place. Holes 34 are conical in shape. This permits the screws to be introduced at angles other than ninety degrees. Typically, the screws are inserted through a trocar 39 or similar device using a cannula. The shape of holes 34 and the alignment between holes 34 and screw holes 36 aid the user in locating trocar 39 relative to screw holes 36.

Bone fixation device holder 32 is configured and dimensioned to releaseably engage bone fixation device 38, i.e., firmly holding bone fixation device 38 while the user is positioning bone fixation device 38, yet also enabling fixation device 38 to be easily separated from holder 32 after fixation device 38 has been screwed into place. FIG. 3 illustrates a preferred structure for releaseably engaging fixation device 38. A bottom side of holder 32 has a recessed area with a width W. As width W is slight smaller than the width of fixation device 38 and, as discussed more fully below, holder 32 is made of a resilient material, fixation device 38 snaps into the recessed area. After fixation device 38 has been screwed into place, fixation device 38 snaps out of the recessed area without altering the position of fixation device 38. As fixation devices are generally rectangular, bone fixation device holder 32 is illustrated as substantially rectangular in nature. However, bone fixation device holder 32 can be made in any shape to accommodate non-rectangular bone fixation devices.

While bone fixation device holder 32 is illustrated as extending the entire length of bone fixation device 38, it may be desirable for holder 32 to extend less than this full length and only align with a limited number of holes. Since fixation devices are manufactured in a variety of lengths, number of holes and hole spacings, a fixation device holder that had only one hole, would be able to interface with a larger variety of fixation devices.

Figure 4:
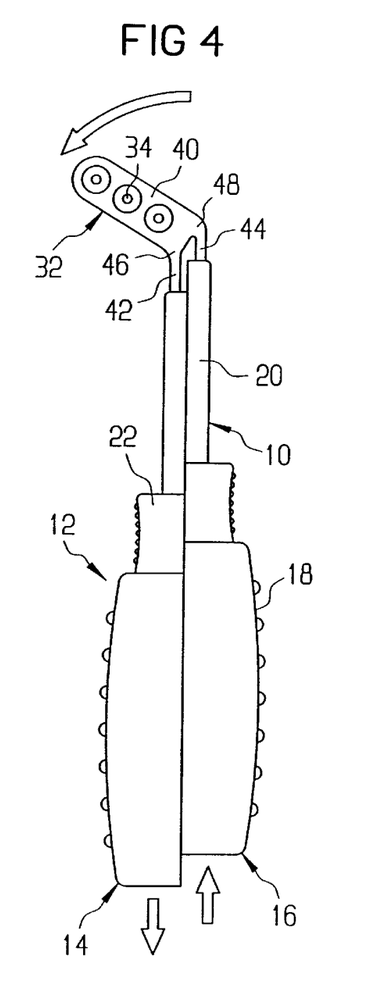
FIG. 4 is a side view of the introducer illustrating the relative movement between the left and right handle portions and the angular motion of the fixation device holder.

As previously discussed, left and right portions 14, 16 of handle 12 are moveable relative to each other. FIG. 4 shows that movement of left portion 14 in a direction proximal to the user, or alternatively, movement of right portion 16 in a direction distal to the user results in counter-clockwise angular movement of bone fixation device holder 32. Similarly, movement of left portion 14 in a direction distal to the user or movement of right portion 16 in a direction proximal to the user results in clockwise angular movement of bone fixation device holder 32. The angular motion is critical when simple manipulation of handle 12 does not provide proper placement of fixation device 38 due to the size and placement of the surgical incision.

Figure 2:
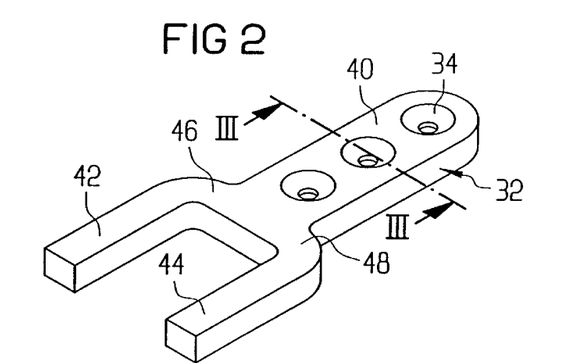
FIG. 2 is a perspective view of one embodiment of a fixation device holder for the introducer.

FIG. 2 illustrates a preferred structure of bone fixation device holder 32 in which the relative movement between left and right portions 14, 16 of handle 12 results in angular movement of holder 32. Holder 32 has a distal segment 40, a left leg 42, and a right leg 44. Distal segment 40 and left and right legs 42, 44 are arranged such that holder 32 is substantially Y-shaped.

Located between distal segment 40 and left leg 42 is left flexible region 46 and located between distal segment 40 and right leg 44 is right flexible region 48. For this invention, flexible regions 46, 48 are preferably a joint of integral design such as a so-called "living hinge." However, any flexible element such as a traditional pin hinge can be used as an alternative to the living hinge so long as relative movement between left and right portions 14, 16 results in the desired angular movement of holder 32.

When left leg 42 is moved in the proximal direction, right flexible region 48 flexes, and, as a result, holder 32 moves in a counter-clockwise direction. When right leg 44 is moved in the proximal direction, left flexible region 46 flexes, and, as a result, holder 32 moves in a clockwise direction. As a proximal end of left leg 42 is connected to a distal end of left portion 14 and a proximal end of right leg 44 is connected to a distal end of right portion 16, relative movement between left and right portions 14, 16 causes the desired angular movement of holder 32.

Bone fixation device holder 32 should be made of material that would permit the functions of releaseably engaging bone fixation device 38 and flexing when left handle portion 14 is moved relative to right handle portion 16. Examples of such a material include metal or a plastic such as nylon, polyethylene, polypropylene, or teflon. Handle 12 can be made of a material such as polycarbonate. Although a metal can be used for handle 12, a polymer or composite based material is preferred as it would result in introducer 10 being lighter in weight.

Figure 5:
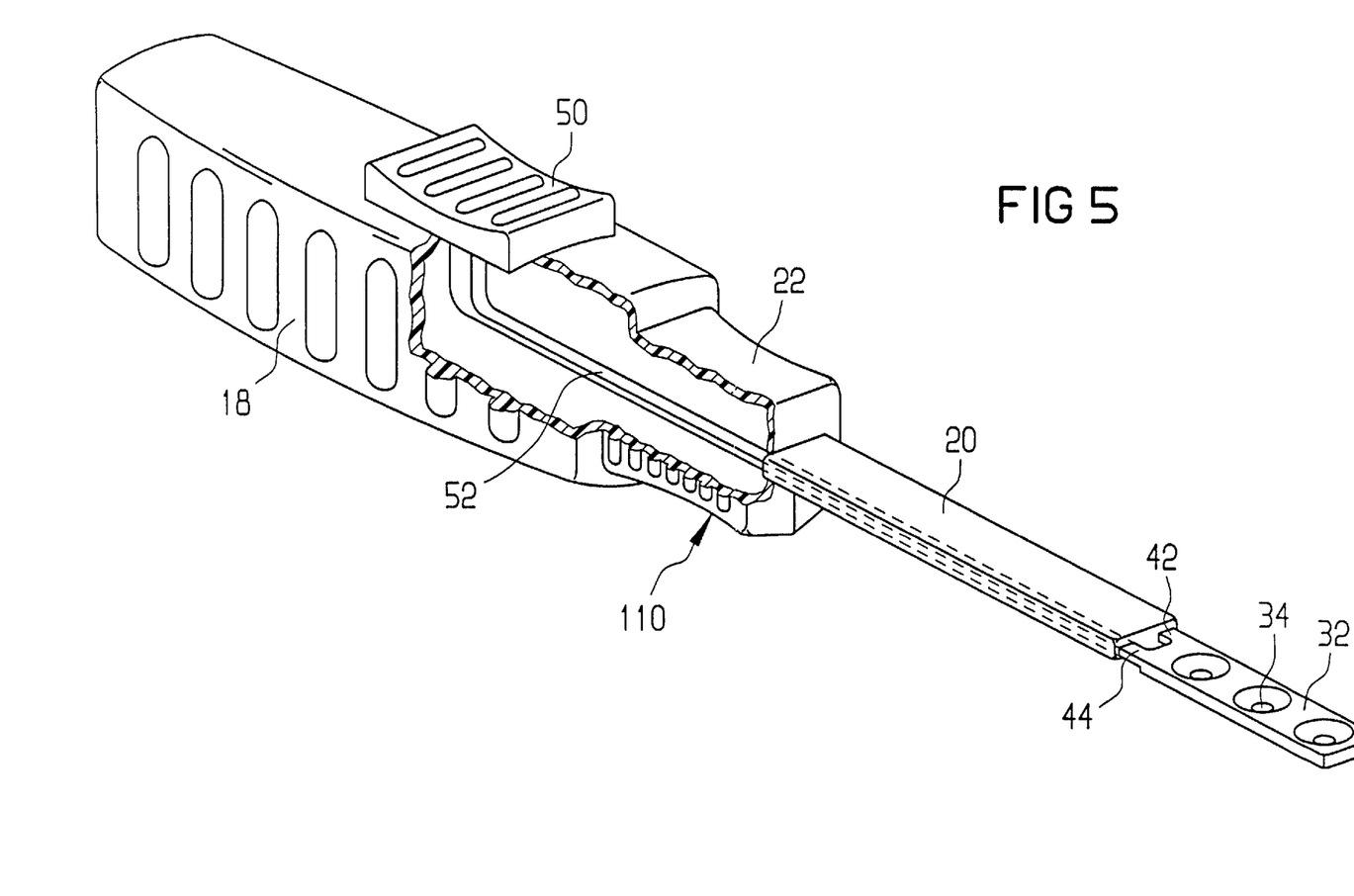
FIG. 5 is a perspective view of a second embodiment of the bone fixation device introducer according to the present invention.

FIG. 5 shows another embodiment of the invention. In FIG. 5, the elements of bone fixation device introducer 110 that are identical to the elements of bone fixation device introducer 10 are designated by the same numeral used in FIGS. 1–4. Furthermore, only those elements of introducer 110 that vary from the analogous element of introducer 10 are discussed in detail.

Handle 12 of introducer 110 has a movable portion 50. Movable portion 50 slides in the proximal/distal direction. A portion of connecting section 22 is cut away to illustrate that internal joining element 52 connects movable portion 50 to right leg 44. As left leg 42 is fixed to extending section 20, sliding movable portion 50 causes angular movement of bone fixation device holder 32. An alternative arrangement would have internal joining element 52 connected to left leg 42 and right leg 44 fixed to extending section 20.

While the movable portion 50 is illustrated as a sliding portion controlled by a thumb, it could alternatively be a trigger controlled by a finger or other similar interface that transmits an implied force to the joining element 52. It should also be noted that while the movable portion is illustrated on the uppermost portion of the handle 12, it could alternatively be disposed on any portion proximal to the bone fixation device holder 32.

Figure 6:
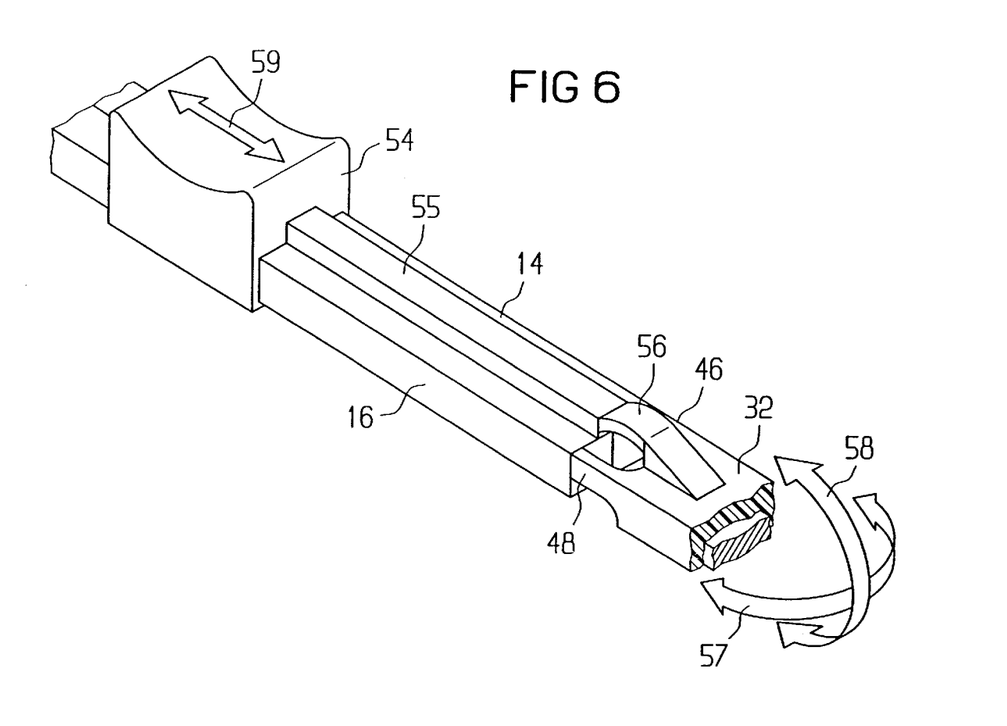
FIG. 6 is a perspective view of a portion of a third embodiment of the bone fixation device introducer according to the present invention.
Figure 7:
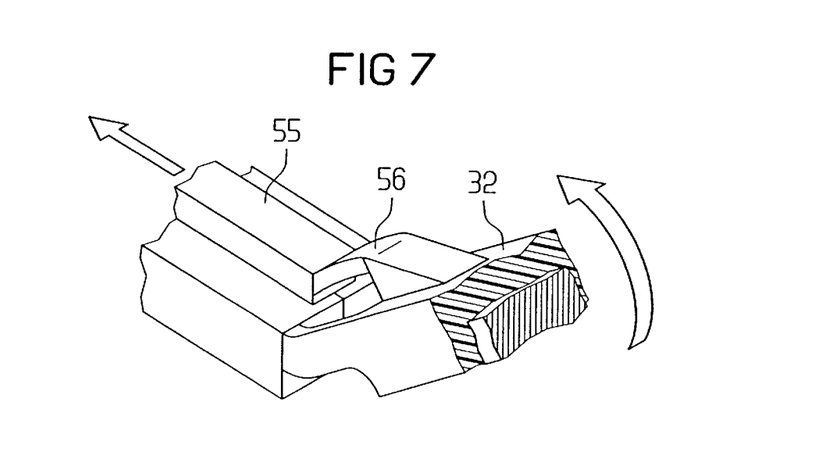
FIG. 7 is a perspective view of a portion of FIG. 6.

Angular movement of bone fixation device holder 32 need not be limited to one plane of motion. FIG. 6 illustrates another embodiment whereby a third flexible region 56 is located between and superior to flexible regions 46 and 48. Flexible region 56 is attached to and controlled by actuating mechanism 54 via a connecting element 55. Translation of the actuating mechanism 54 along a vector 59 in a distal/proximal direction results in angulation of holder 32 in a plane 58 perpendicular to plane 57. Plane 57 is the plane in which the holder angulates when left and right portions 14 and 16 are translated in a distal/proximal direction as discussed previously. FIG. 7 illustrates holder 32 angulated in plane 58. It is possible for the holder 32 to simultaneously angulate in planes 57 and 58 allowing for the holder 32 to articulate in a spatial orbit providing a greater degree of control of holder 32.

Figure 8:
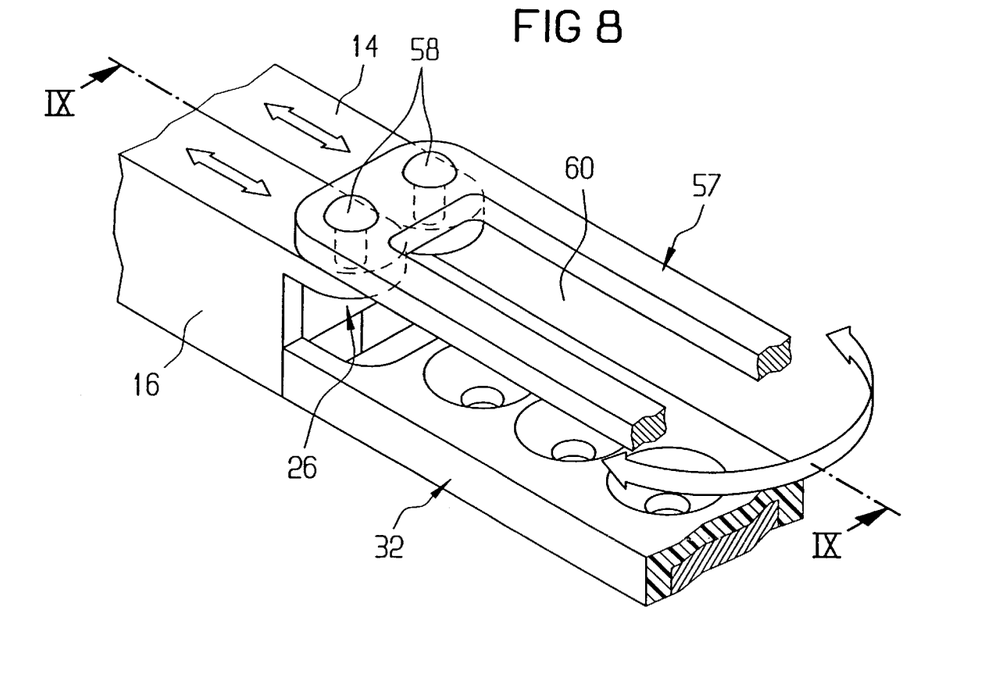
FIG. 8 is a perspective view of a portion of a fourth embodiment of the bone fixation device introducer according to the present invention.
Figure 9:
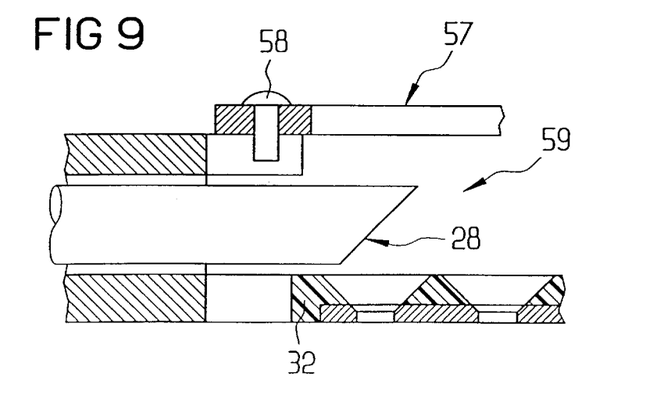
FIG. 9 is a cross-sectional view of a portion of the fourth embodiment of the bone fixation device introducer, taken along line IX—IX of FIG. 8.

FIG. 8 illustrates another embodiment whereby a tissue retractor element 57 is attached to left and right portions 14 and 16 through flexible joints 58. Relative movement of left and right portions 14 and 16 cause angular movement of holder 32 as well as coincident angular movement of retractor element 57. As illustrated in FIG. 9, this retractor element 57 provides an optical cavity 59 so that the endoscope 28 has an unimpaired view of fixation device holder 32. Retractor element 57 is shown with a slot 60 along its length to allow access to the screw holes from the top. The shape and contour of retractor element 57 can be varied to accommodate varying soft tissue constraints. While flexible joints 58 are illustrated as pins, a number of flexible joint designs would work as well.

Figure 10:
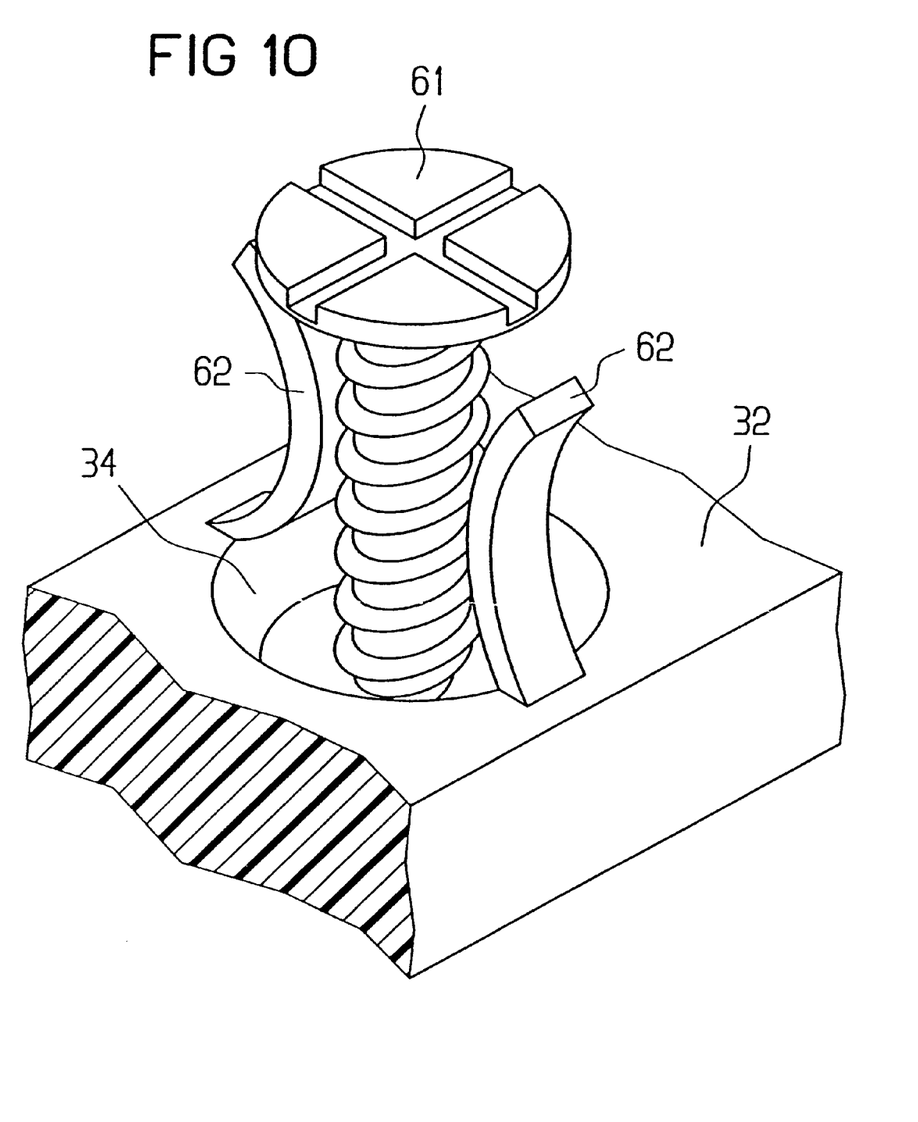
FIG. 10 is perspective view of one embodiment of a mechanism for holding a bone screw in alignment with a screw hole of the bone fixation device.

FIG. 10 illustrates another structure of bone fixation device holder 32 whereby screw 61 or other fixation hardware is retained by retaining element 62. Concentric alignment of screw 61 relative to hole 34 is maintained by retaining element 62. Retaining element 62 holds the threaded portion of screw 61 while screw 61 is initially being driven. Once screw 61 has engaged the bone, the flexible design of retaining element 62 would allow passage of the larger diameter screw head. If screw 61 was of a self-drilling style, bone fixation device 38 could be attached without the need for predrilling the bone.

The preferred embodiments disclosed above discuss the present invention using endoscopic procedures as an example of one application. However, the introducer according to the present invention can be used in any surgical procedure to assist the implantation of a bone fixation device.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A bone fixation device introducer comprising:
   a bone fixation device holder for releasably engaging a bone fixation device having screw holes, the holder having at least one hole configured and dimensioned such that the at least one hole is larger in diameter than the bone fixation device screw holes and is positioned for alignment with at least one of said screw holes when the bone fixation device is engaged by the bone fixation device holder; and
   a handle operatively associated with the bone fixation device holder and positioned proximally thereto, the handle having at least two portions slidably connected to each other, whereby sliding movement of one handle portion relative to the other handle portion results in an angular movement of at least a portion of the holder relative to the handle for control over the positioning and placement of the bone fixation device.

2. The introducer of claim 1, wherein the bone fixation device holder is made of plastic and includes a recessed area which releaseably engages the bone fixation device.

3. The introducer of claim 2, wherein the recessed area of the bone fixation device holder has a width that is slightly less than the bone fixation device width so that the bone fixation device is held in frictional engagement within the recessed area of the bone fixation device holder.

4. The introducer of claim 1, wherein the bone fixation device holder has a distal segment which contains the at least one hole and a proximal segment having two legs for connection to the handle.

5. The introducer of claim 4, wherein one leg of the bone fixation device holder is connected to the one handle portion by a joining element and the other leg is directly connected to the other handle portion.

6. The introducer of claim 1, wherein the handle has at least one bore for receiving an endoscope.

7. The introducer of claim 1, wherein the at least one hole is substantially conical in shape.

8. The introducer of claim 1, whereby the sliding movement of the at least two handle portions results in movement of a tissue retraction element such that the movement of the tissue retraction element is coincident with the movement of the holder.

9. A bone fixation device introducer comprising:
   a bone fixation device holder for releaseably engaging a bone fixation device having screw holes, the holder having a plurality of spaced holes configured and dimensioned such that the spaced holes are larger in diameter than the bone fixation device screw holes and are positioned for alignment with said screw holes when the bone fixation device is engaged by the bone fixation device holder; and
   a handle operatively associated with the bone fixation device holder and positioned proximally thereto, the handle having left and right portions slidably connected to each other,
   whereby sliding movement of the left and right portions of the handle relative to each other results in an angular movement of at least a portion of the holder relative to the handle for control over positioning and placement of the bone fixation device.

10. The introducer of claim 9, wherein the bone fixation device holder is made of plastic and includes a recessed area which releaseably engages the bone fixation device.

11. The introducer of claim 10, wherein the recessed area of the bone fixation device holder has a width that is slightly less than the bone fixation device width so that the bone fixation device is held in frictional engagement within the recessed area of the bone fixation device holder.

12. The introducer of claim 9, wherein the bone fixation device holder has a distal segment which contains the spaced holes and a proximal segment having two legs for connection to the handle.

13. The introducer of claim 12, wherein one leg of the bone fixation device holder is connected to the right portion of the handle and the other leg is connected to the left portion of the handle such that movement of the left and right portions of the handle results in movement of the holder.

14. The introducer of claim 13, wherein each leg is connected to the handle portion by a flexing element, whereby relative movement of the left and right portions of the handle results in bending of the flexing element to cause angular movement of the holder.

15. The introducer of claim 9, wherein the handle has at least one bore for receiving an endoscope.

16. The introducer of claim 9, wherein the spaced holes are substantially conical in shape.

17. The introducer of claim 9, whereby the relative movement of the left and right portions results in movement of a tissue retraction element such that the movement of the tissue retraction element is coincident with the movement of the holder.

18. The introducer of claim 9, wherein the bone fixation device holder has a mechanism for releaseably engaging bone screws such that the bone screws are retained in position aligned to enter the spaced holes of the bone fixation device holder and through the screw holes of the bone fixation device.

* * * * *